United States Patent
Schwendele et al.

(10) Patent No.: US 12,042,129 B2
(45) Date of Patent: Jul. 23, 2024

(54) STOPCOCK FOR AN ENDOSCOPE

(71) Applicant: OLYMPUS WINTER & IBE GMBH, Hamburg (DE)

(72) Inventors: Andrea Schwendele, Hamburg (DE); Hannes Miersch, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 421 days.

(21) Appl. No.: 17/154,322

(22) Filed: Jan. 21, 2021

(65) Prior Publication Data

US 2021/0219826 A1    Jul. 22, 2021

(30) Foreign Application Priority Data

Jan. 20, 2020 (DE) ...................... 10 2020 101 206.3

(51) Int. Cl.
*A61B 1/015* (2006.01)
*A61B 1/00* (2006.01)
*A61B 1/12* (2006.01)

(52) U.S. Cl.
CPC .......... *A61B 1/015* (2013.01); *A61B 1/00068* (2013.01); *A61B 1/00073* (2013.01); *A61B 1/00137* (2013.01); *A61B 1/121* (2013.01)

(58) Field of Classification Search
CPC ........... A61B 1/015; A61B 1/12; A61B 1/121; A61B 1/00137; F16K 5/0207; F16K 5/02; F16K 5/0271
See application file for complete search history.

(56) References Cited

U.S. PATENT DOCUMENTS

| | | | |
|---|---|---|---|
| 3,779,513 A * | 12/1973 | Levine | F16K 5/0292 251/309 |
| 6,012,702 A | 1/2000 | Heimberger | |
| 9,791,061 B2 * | 10/2017 | Pippel | F16B 21/125 |
| 10,969,022 B2 * | 4/2021 | Miersch | F16K 5/165 |
| 2002/0179878 A1 * | 12/2002 | Nosel | F16K 5/02 251/309 |
| 2019/0234518 A1 | 8/2019 | Miersch | |

FOREIGN PATENT DOCUMENTS

| | | |
|---|---|---|
| CN | 109690154 A | 4/2019 |
| DE | 4226770 A1 | 5/1994 |
| DE | 10126540 A1 | 12/2002 |
| DE | 102014002158 B4 | 2/2019 |
| DE | 102019203684 A1 | 9/2020 |

* cited by examiner

*Primary Examiner* — Matthew J Kasztejna
(74) *Attorney, Agent, or Firm* — Oliff PLC (57) ABSTRACT

A stopcock for a liquid channel of a medical endoscope, having a housing, a spring element and a plug rotatably mounted in the housing, wherein the plug in a working position lies with its conical surface against a seal surface of the housing and can be placed in a medium access position in which the conical and the seal surface have no contact and the housing and the plug remain connected, characterized in that the plug includes one or more transverse grooves, in the outer wall of a conical piece, running transversely to the longitudinal axis of the conical piece and having straight groove bottoms, and the spring element in the medium access position engages with one or more transverse grooves. A medical endoscope having at least one liquid channel, characterized in that it includes at least one stopcock, by which the liquid flow through the channel can be regulated.

10 Claims, 6 Drawing Sheets

STOPCOCK FOR AN ENDOSCOPE

BACKGROUND

The invention relates to stopcocks for a liquid channel of a medical endoscope as well as medical endoscopes.

Medical endoscopes are instruments with an elongated, tubular, flexible or rigid shaft and an optics, which are used for minimally invasive investigation of interior spaces of the human body and for minimally invasive procedures. Through the shaft segment of the endoscopes, penetration instruments such as stone baskets, instruments for electrosurgical resectioning, or forceps can be taken to the treatment site. In order to flush away any local bleeding occurring during the procedure and to protect the tissue against heat injury, for example, due to a high-frequency electrosurgical application, the endoscopes are often provided with a flushing device, which constantly flushes the tissue situated in front of the distal shaft end. The flushing liquid can be taken through corresponding separate liquid channels, through the inner tube or through the casing tube. In order to control the inflow and outflow of the liquid, the liquid channels generally have a stopcock at their proximal end region. Corresponding stopcocks are described for example in DE 101 26 540 A1 and DE 10 2014 002 158 B4.

The stopcocks usually consist of a housing and a plug rotatable therein, whose walls border on each other in a sealing manner. The large contact surface between housing and plug is hard to clean and sterilize in the assembled state, since the spacing between the two pieces is too small to be reached reliably by the steam during the autoclaving.

Therefore, at present the plug needs to be loosened or unlocked by a screw and removed from the housing. This opens the critical gap between the two pieces, so that the steam can reach the surfaces unhindered during the autoclaving. After the autoclaving, the instrument must then be put together once more, making the preparation time prior to the operation a long one. Some instruments possess up to four different stopcocks, whose plugs need to be matched up with the proper liquid channels once more after such a disassembly and cleaning. It may therefore take some time before all the stopcocks of an endoscope are again assembled and ready to use after the cleaning. What is more, the plugs are often relatively small, so that there is a risk of losing them during an autoclaving process—especially when autoclaving several endoscopes at the same time.

In U.S. Pat. No. 6,012,702, in order to assure the sterilizability of all surfaces and to prevent a loss of the plug during the cleaning, a two-stage flexible locking of the plug in the stopcock housing is proposed. For this, the plug comprises two parallel annular grooves running concentrically about its longitudinal axis. The plug is locked to the housing in its working position by form fitting and force locking. In this working position, seal surfaces of the plug lie tightly against seal surfaces of the housing and an annular spring lies in the first annular groove. By overcoming the locking, the plug can be moved into an intermediate position, in which the seal surfaces are not in contact and the annular spring lies in the second groove. In the intermediate position, sterilization gas can flow through the gap between the seal surfaces, so that a deficient sterilization is prevented.

The drawback to this design, however, is that the locking geometries for the working position and the intermediate position are identical and the two positions can only be distinguished with difficulty. This increases the risk of sterilizing in the working position or working in the intermediate position.

Hence, there is a need for stopcocks for endoscopes which can be cleaned easily and trouble-free, having no risk of loss or mixing up of their plugs during the following assembly process, and in which the working position and sterilization position are easy to distinguish.

Specification

This problem is solved by a stopcock having the features of the disclosed embodiments and an endoscope having the features of the disclosed embodiments. According to the invention, it is provided in particular that there is formed in the conical surface of the plug a transverse groove, having a straight groove bottom.

In a first aspect, the invention relates to a stopcock for a liquid channel of a medical endoscope, having a housing, a spring element and a plug rotatably mounted in the housing, wherein the plug in a working position lies with its conical surface against a seal surface of the housing and can be placed in a medium access position in which the conical surface and the seal surface have no contact and the housing and the plug remain connected, characterized in that the plug comprises one or more transverse grooves, in the outer wall of a conical piece, running transversely to the longitudinal axis of the conical piece and having straight groove bottoms, and the spring element in the medium access position engages with the one or more transverse grooves.

The stopcock according to the invention is suited to ensuring that the stopcock remains in the medium access position and open during the sterilization, so that sterilization gas can penetrate along the gap between the plug cone and the housing. The medium access position is easily recognizable to the medical staff and the cleaning personnel in that the stopcock cannot be closed, or only closed with great difficulty, in this position.

The stopcock according to the invention is moreover suited to regulating the liquid flow in a liquid channel. By turning the plug of the stopcock about its axis of rotation, the liquid flow through the liquid channel can be reduced and stopped entirely (closed position). For this purpose, the liquid channel runs through the stopcock, i.e. the stopcock comprises a liquid channel in its interior, whose diameter is substantially equal to that of the respective channel in the endoscope. The open position of the stopcock means according to the invention the position in which the stopcock is fully open, i.e. in which the maximum quantity of liquid can flow through the stopcock.

The stopcock comprises a housing (stopcock housing), a spring element and a plug, or it consists of these three elements. The plug can be locked with the housing and the spring element in two positions, a working position and a medium access position (also the cleaning position or sterilization position). The term "medium" in this context means in particular sterilization and cleaning liquids and gases. The term "access" means that these liquids and gases can get in between the plug and the housing in this position, especially between the seal surfaces and conical surfaces. In other words, the plug can be placed in a working position and a medium access position. In both positions, the plug, the housing and the spring element are locked to each other. Thus, the stopcock cannot fall apart during the cleaning.

In the working position, the plug lies with its conical surface against a seal surface of the housing. The conical surface lies here tightly, i.e. preferably liquid-tight, more preferably also substantially gas-tight, against the seal surface of the housing. Preferably, no liquid and/or gas can get through to the outside of the stopcock from the liquid channel between the plug and the housing. Therefore, the seal surface and the conical surface preferably lie against each other along the entire circumference of the conical piece and both on the handle side and on the side of the liquid channel facing away from the handle. In the working position, the plug and the housing are locked to each other. The working position can also be called a first locking position.

In the medium access position, the conical surface and the seal surface are not in contact. A liquid and gas entry between the conical surface and the seal surface is thus possible and desirable. Preferably, liquid and/or gas can get through to the outside of the stopcock from the liquid channel between the plug and the housing. The gap existing between the conical surface and the seal surface in the medium access position is thus large enough to ensure the sterilizability of the two surfaces. As described above, however, the housing and the plug remain locked together. The medium access position can also be called a second locking position.

Basically, the stopcock can be placed in the open position (liquid channel open) and in the closed position in both the working position and in the medium access position. This is generally done by rotating the plug about the longitudinal axis of its conical piece, for example by using a handle part. In order to achieve an especially good cleaning effect, however, the stopcock is preferably in the open position during the cleaning.

The plug comprises, one behind the other in the direction of its axis of rotation, a conical piece and a handle part. The plug is mounted rotatably in the housing. The conical piece of the plug is shaped as a truncated cone with a liquid channel passing through it, whose longitudinal axis runs transversely to the axis of rotation of the plug. The outer wall of the conical piece here means its lateral surface. The end face of the conical piece facing away from the handle part is not viewed as being part of the outer wall here. The outer wall of the conical piece therefore encompasses the conical surface which can be placed in sealing manner against the seal surface of the housing. The conical surface thus constitutes at least part of the lateral surface of the conical piece.

The plug comprises one or more transverse grooves, in the outer wall of the conical piece, running transversely to the longitudinal axis of the conical piece and having straight groove bottoms. The transverse grooves are suited to receiving a segment of the spring element in a locking position (medium access position). Accordingly, they are formed at least partly complementary in size to the segment. The transverse groove may have a polygonal, a partially circular, a U-shaped, or a trapezoidal cross section, preferably a substantially trapezoidal cross section, i.e. a cross section with an outwardly sloping wall.

For example, the plug may comprise one, two, three or four transverse grooves, two transverse grooves being preferred. If the plug has more than one transverse groove, they are preferably arranged in pairs, so that each time the two transverse grooves of a pair are opposite each other on the conical piece. In one embodiment, the plug thus has two transverse grooves, preferably being opposite each other on the conical piece.

The transverse grooves each run transversely to the longitudinal axis of the conical piece. This means that the longitudinal axis of the transverse groove is arranged transversely to the longitudinal axis of the conical piece.

Furthermore, the transverse grooves according to the invention are preferably arranged on the plug such that the spring element described elsewhere herein or a segment of the spring element can lie in them when the stopcock is in an open position. Accordingly, in the open position, the longitudinal axis of the transverse groove is parallel to the longitudinal axis of the segment of the spring element.

Hence, the transverse grooves ensure that the stopcock remains in the open position during the sterilization of the instrument. Preferably, the stopcock is in the open position in the medium access position, and preferably it cannot be placed in the closed position in the medium access position, or only by exerting a force which is greater than that to rotate the stopcock in an entirely concentric groove, such as the first annular groove. The force needed to place the plug in the closed position in the medium access position is preferably at least twice as large as the force needed to rotate the plug into the closed position in the working position.

This is accomplished by the straight configuration of the groove bottom of the transverse groove. Unlike the concentrically running annular grooves, the transverse groove does not run around the conical piece but instead it is straight on one side of the conical piece. This produces a protrusion in the lateral surface of the conical piece at the groove ends, which has to be overcome by the spring element when the plug is rotated, exerting a larger force. According to the usual understanding of the term, the feature "groove bottom" is the inner side of the groove, which is opposite its open side—that is, the side provided for the engaging of the spring element. This should be distinguished from the inner sides situated laterally to the groove bottom, representing the connection between the open side and the groove bottom.

The plug will generally comprise a first concentrically running annular groove parallel to the transverse groove. The spring element in the working position will engage with this annular groove. In this way, the plug will be locked in the housing in the working position. The annular groove thus forms a recess in the lateral surface of the conical piece running in a circular manner about the longitudinal axis of the conical piece. Preferably, the annular groove has a regular formation, i.e. the cross section of the annular groove is identical in size and shape, or substantially identical, along the entire length of the annular groove. The first annular groove may comprise cross section shapes as indicated above for the transverse groove, wherein a substantially funnel-shaped cross section shape is preferred for the first annular groove.

The first annular groove is separated from the transverse groove by an annular shoulder on the plug. The first annular groove is preferably arranged between the handle part of the plug and the transverse groove on the conical piece. However, a reverse arrangement, in which the transverse groove is situated between the first annular groove and the handle part, is likewise conceivable. In the former embodiment, the transverse groove is situated in a portion of the conical piece having a smaller diameter than the portion in which the annular groove is situated. In the latter embodiment, the transverse groove is situated in a portion of the conical piece having a larger diameter than the portion in which the first annular groove is situated.

The one or more transverse grooves may be configured each as a segment of a second annular groove, wherein the second annular groove runs concentrically parallel to the first annular groove outside of the one or more transverse grooves. The second annular groove prevents the plug from falling out when the plug is rotated from the medium access position to the working position. The second annular groove may be configured in the same way as described above for the first annular groove in areas where it is not intersected by the one or more transverse grooves.

Alternatively or additionally, the plug may comprise one or more connection grooves in the outer wall of its conical piece, each of them joining one end of a transverse groove to the first annular groove. The one or more connection grooves are spiral in shape and have the effect of automatically locking the plug in the open position when it is moved into the medium access position. The connection grooves may accordingly also be called thread grooves. Preferably, the number of connection grooves is equal to the number of transverse grooves.

The one or more connection grooves are arranged at a slant to the longitudinal axis of the first annular groove. These preferably start from the end of a transverse groove situated in the direction of rotation of the plug and run at a slant in the direction of rotation toward the first annular groove. The "direction of rotation" here means the direction in which the plug must be turned about its longitudinal axis in order to rotate the stopcock from the open position to the closed position.

The housing of the plug may be formed as a single piece with a shaft segment of the endoscope or it may be introduced into the endoscope as a separate piece. The housing generally has a typical cuboidal shape, which can accommodate the conical piece of the plug in its interior. For this purpose, the housing moreover has an interior conical cavity, being open at least at one end for the introducing of the plug. The cavity is substantially complementary in diameter to the conical piece of the plug, especially complementary to the diameter of the plug, as measured at its sealing conical surfaces. After introducing the plug into the housing, the conical surfaces of the plug therefore border on the inner walls of the cavity when the stopcock is in its working position, i.e. when the spring element engages with the first annular groove. The sealing sections of the inner walls, bordering on the conical surfaces of the plug in the working position, are therefore called here the seal surfaces of the housing. On the other hand, in the medium access position, i.e. in the position in which the spring element engages with the transverse groove, a gap exists between the seal surfaces and the conical surfaces.

The cavity of the housing furthermore has at least one annular shoulder, which runs concentrically about the longitudinal axis of the cavity or the conical piece of the plug. The annular shoulder in the working position of the stopcock engages with the transverse groove. It may therefore be formed complementary in shape and size to the transverse groove or to the connection formed by the transverse groove and the second annular groove. In the medium access position of the stopcock, the annular shoulder may be arranged for example on the end face of the conical piece.

The stopcock according to the invention moreover comprises a spring element, arranged between the housing and the plug. The spring element is suited to locking the plug inside the housing. For this, the spring element exerts a spring force in the direction of the longitudinal axis of the conical piece. In the working position and the medium access position, the spring element engages respectively with the first annular groove and the transverse groove(s). Thus, in particular, the spring element in the medium access position engages with the one or more transverse grooves. During the transition from one position to another, the spring element is compressed.

The spring element may be for example a bending spring or an elastomer ring, bending springs being preferred. In any case, the spring element is able to exert a spring force on two oppositely situated sides of the conical piece, the spring force acting respectively in the direction of the longitudinal axis of the conical piece. The bending spring can be made, e.g., from stainless spring steel or a non-ferrous metal. Preferably, the bending spring has a round cross section (a wire spring).

The spring element is preferably secured in the housing. The securing is such that the spring element cannot easily drop out from the housing when no plug is situated inside the housing.

In a second aspect, the invention relates to a medical endoscope having at least one liquid channel, characterized in that it comprises at least one stopcock according to the invention, by means of which the liquid flow through the liquid channel can be regulated. "Regulated" in this context means that the position of the plug in the stopcock can regulate whether or not liquid can flow through the stopcock. In an open position of the stopcock, liquid can flow through the stopcock, while in a closed position no liquid can flow through the stopcock. Preferably, furthermore, the volume of the liquid flow can also be reduced by gradually closing the stopcock.

The medical endoscope is preferably a gynecological or urological endoscope. The endoscope may be, e.g., a resectoscope, hysteroscope, ureteroscope, arthroscope or cystoscope. Alternatively, the endoscope may also be a gastroscope, coloscope or bronchoscope. Whereas the former are usually provided with a rigid shaft piece, the latter usually have a flexible shaft piece. The endoscope may be designed as a resectoscope.

The endoscope comprises, in the typical manner of endoscopes, an elongated, tubular shaft piece. The shaft piece or the shaft tube of the endoscope may have a length, e.g., of at least around 150 mm, for example a length between 150 mm and 400 mm. The shaft diameter may be, e.g., around 3 to 10 mm. This produces a very long and thin configuration of the shaft tube. Besides this shaft piece, the resectoscope has a handle system for holding and operating the unit, usually consisting of two handle parts.

The endoscope comprises at least one liquid channel, for example, one, two, three, four or more liquid channels. A liquid channel may be formed by a flushing tube, interior tube, casing tube or the like. In order for the medical staff to have a clear view of the treatment area during the procedure thanks to the optics, a flushing liquid is brought during the procedure through the liquid channel into the interior of the body or taken away through the liquid channel. With this flushing liquid, it is possible to flush away pieces of tissue that are loosened during a resectoscopy, for example. Furthermore, the flushing liquid serves for removing cloudiness from the viewing field of the optical image conductor, such as that caused by blood.

For the supply of liquid, a liquid channel can generally be associated with a flushing device or a pump in the proximal region of the endoscope, so that the flushing liquid can be supplied at first with a predeterminable pressure to the interior of the body. The drainage of excess liquid will generally occur spontaneously through a liquid channel. However, it is also possible to ensure the drainage by applying a slight partial vacuum to the liquid channel.

Moreover, a stopcock according to the invention is arranged in or on the liquid channel in the proximal end region of the endoscope for regulating the flow of liquid. This is preferably also arranged in the proximal end region of the liquid channel, for example at its proximal end. Thus, for example, the stopcock can be held shut when no pump or other liquid supply is as yet connected to the liquid channel. The proximal end region may be angled relative to the main part of the liquid channel. The stopcock for example can be fashioned as a separate part, having connection elements on both sides for connecting to a liquid channel or an endoscope or to a liquid supply or drainage.

Besides the liquid channel or channels, the endoscope may encompass further components, such as an optical image conductor, fiber optical bundle, one or more working channels and penetration instruments, such as an electrode instrument.

In yet another aspect, the invention also relates to the plug described herein.

BRIEF DESCRIPTION OF THE FIGURES

The drawings present exemplary embodiments of the invention in schematic fashion. There are shown.

EXEMPLARY EMBODIMENTS

Further benefits, characteristics and features of the present invention will be made clear in the following detailed description of exemplary embodiments with the aid of the enclosed drawings. However, the invention is not limited to these exemplary embodiments.

Figure 1:
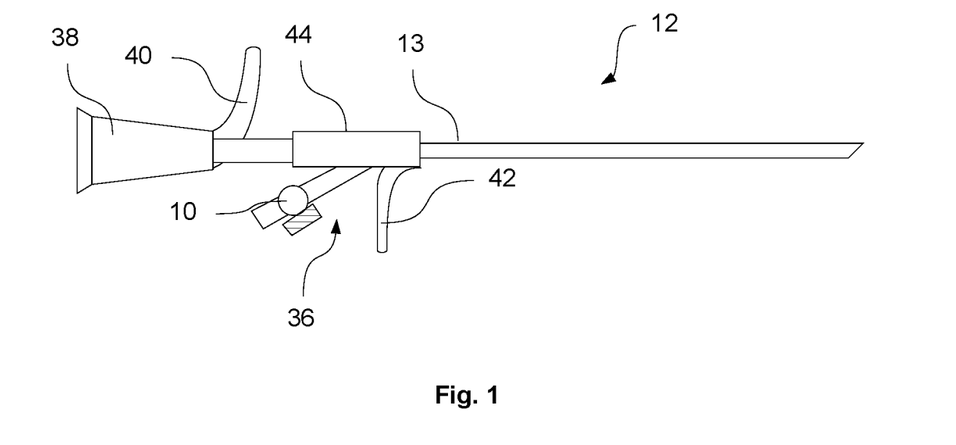
FIG. 1 a schematic side view of an endoscope according to the invention, comprising a stopcock.

FIG. 1 shows a schematic side view of an endoscope 12 according to the invention, comprising a stopcock 10. The endoscope 12 comprises a liquid channel 11 running inside the shaft piece 13, not visible here, which leads through a main body 44 at an angle to an inlet connection 36. At the inlet connection 36 there is arranged a stopcock 10 to regulate the flow of liquid through the liquid channel 11. A pump for supplying liquid to the liquid channel 11 may be connected at the inlet connection 36, for example.

The side view shown here shows the medical endoscope 12 in the orientation in which it is normally used during an operation. The endoscope 12 has at its proximal end an eyepiece 38 for observation of the operating area. In order for the operator to securely hold the endoscope 12 during the operation, there are two grip pieces 40, 42 secured to the endoscope 12. The grip pieces 40, 42 are ergonomically shaped, as usual, so that the operator can hold the endoscope 12 in one hand with the aid of the grip pieces 40, 42. The other hand of the operator is free, for example, to introduce and operate penetration instruments in a working channel of the instrument.

Figure 2:
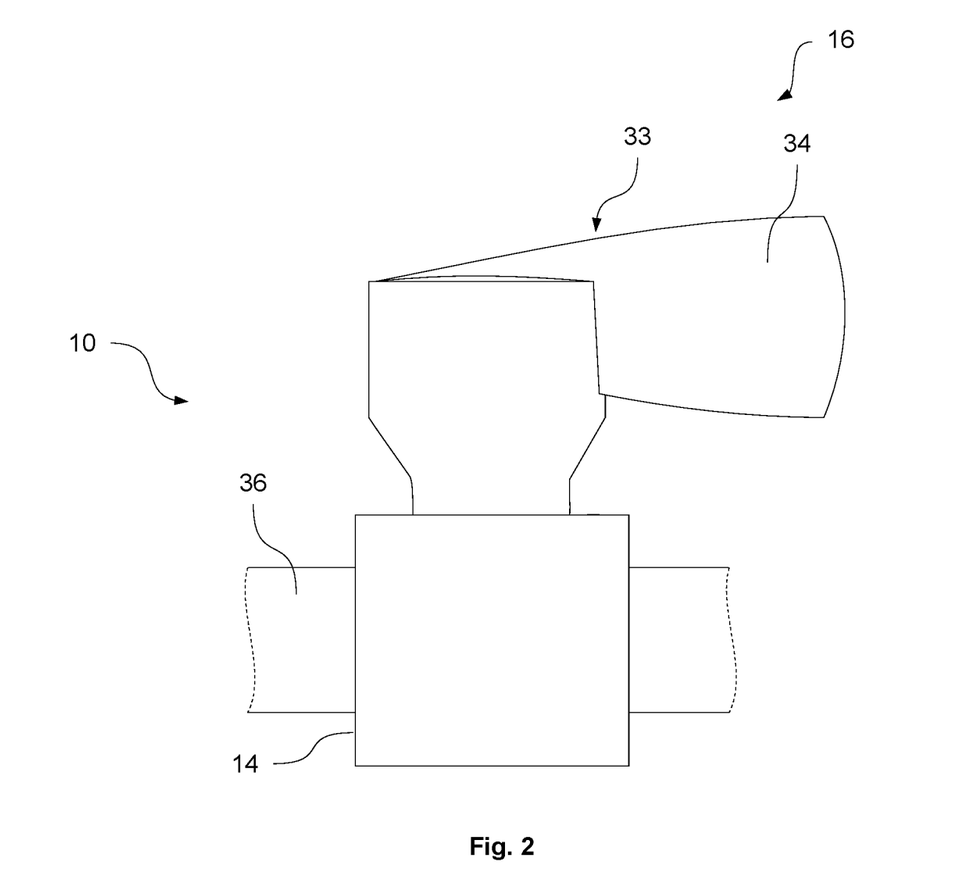
FIG. 2 a schematic side view of an endoscope according to the invention.
Figure 5:
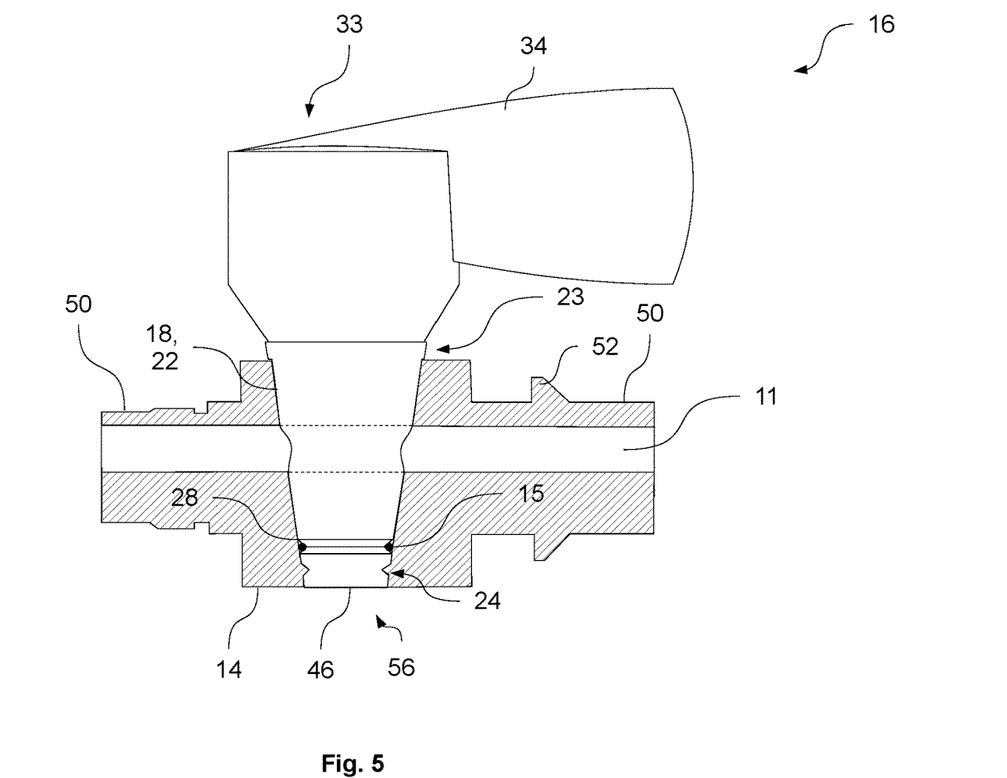
FIG. 5 a schematic cross-sectional side view of the stopcock according to the invention, the stopcock being in the working position and the open position.
Figure 7:
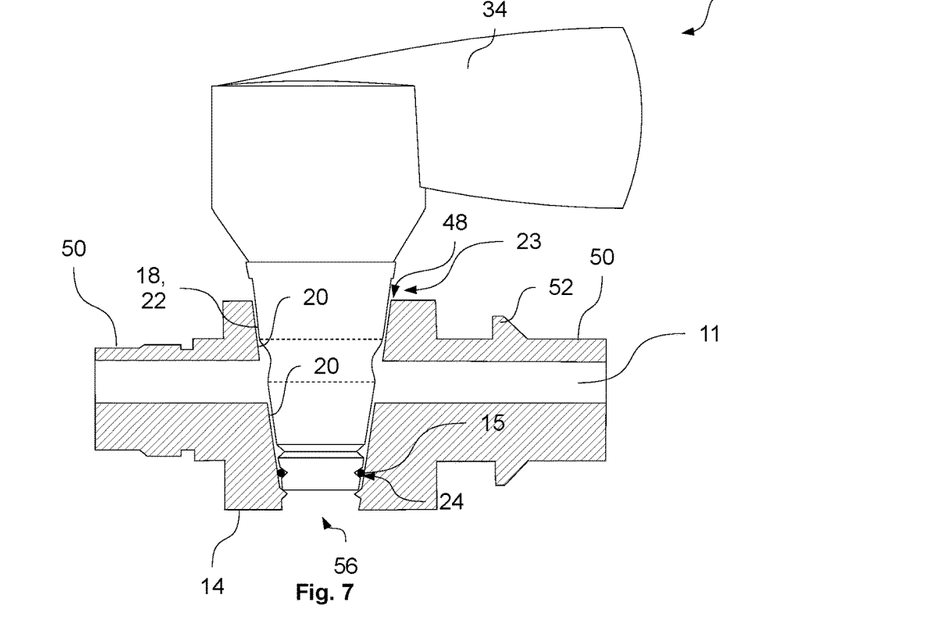
FIG. 7 a schematic cross-sectional side view of the stopcock according to the invention, the stopcock being in the medium access position and the open position.

FIG. 2 shows a schematic side view of a stopcock 10 endoscope according to the invention, comprising a housing 14 and a plug 16, which is received in the housing 14 by means of its conical piece 23, not visible here. The housing 14 is roughly cuboidal in shape and makes a single piece with the tubular inlet connection 36. Alternatively, it is also conceivable to provide connection pieces 50 on either end* of the housing 14, as shown in FIGS. 5 and 7, by means of which a connection to an inlet connection 36 can be produced. The housing 14 has a larger circumference and diameter than the rest of the inlet connection 36, in order to accommodate the plug 16.

As can be seen in FIG. 2, the plug 16 comprises a handle 33, having a handle part 34 which can be grasped by the user to rotate the plug 16. The handle part 34 may be ergonomically designed for this purpose, in order to make it easier to be held and moved by the user.

Figures 3, 4:
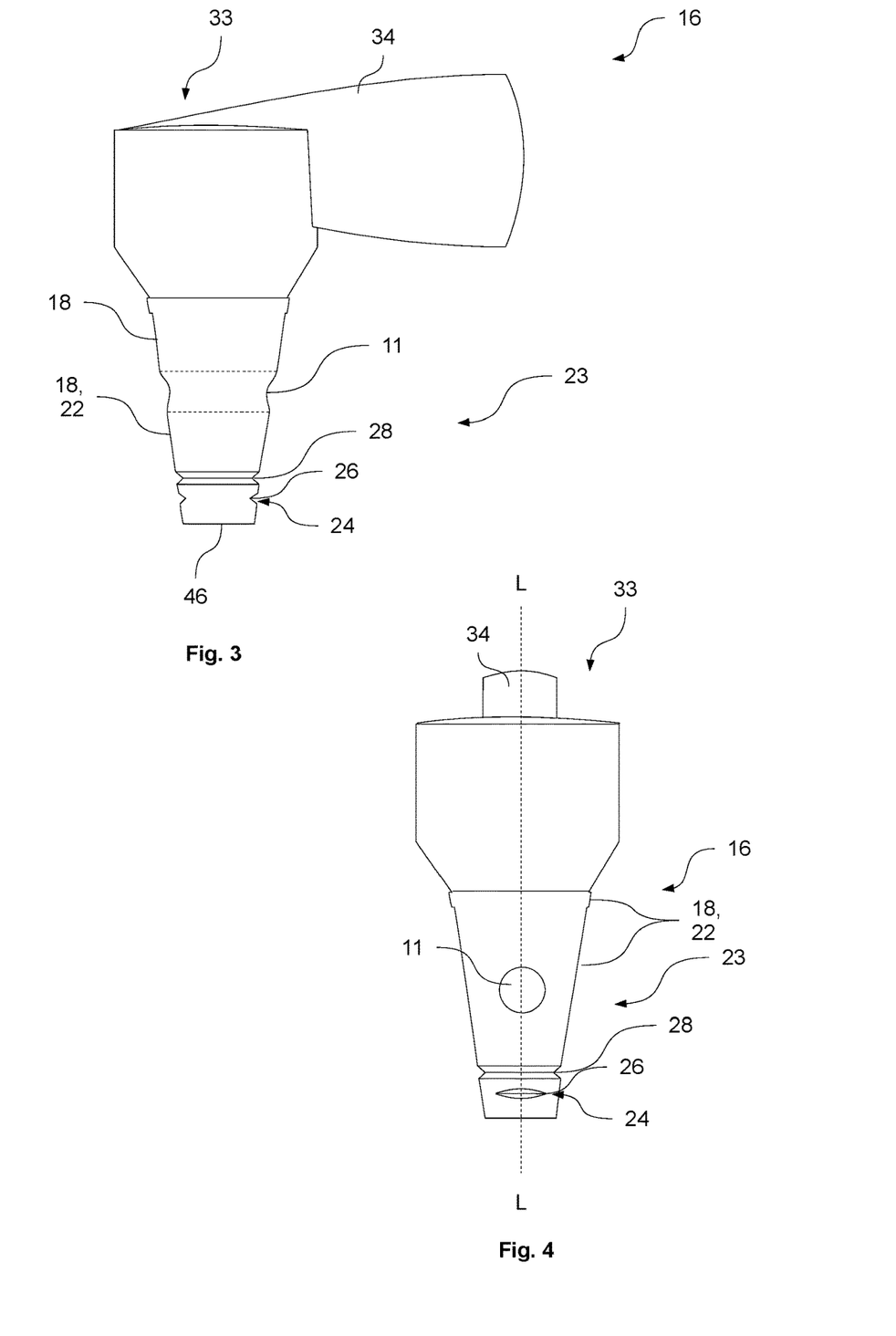
FIG. 3 a schematic side view of a plug according to the invention.
FIG. 4 a further schematic side view of the plug according to the invention from FIG. 3, the plug having been rotated 90° about the longitudinal axis (L) of its conical piece.

FIG. 3 and FIG. 4 show schematic side views of a plug 16 according to the invention, having two transverse grooves 24 in its conical piece 23, running transversely to the longitudinal axis L of the conical piece 23 and having straight groove bottoms 26. The plug 16 in FIG. 4 has been rotated by 90° about the longitudinal axis L of its conical piece (axis of rotation of the plug) as compared to FIG. 3.

The plug 16 consists, first of all, of a conical piece 23, which can be introduced into a housing 14 in order to form a stopcock 10, and a handle 33, having a handle part 34 as described above for easier operation of the stopcock 10.

The conical piece 23 is designed with an outer surface, designated here as the outer wall 22. The outer wall 22 encloses the outer surfaces of the conical piece 23, situated radially to the axis of rotation L, i.e. its side surfaces, but not the end face 46 of the conical piece 23. The outer wall 22 encloses the conical surface 18. The conical surface 18 here means the sealing surface of the outer wall 22, which in the working position lies tightly against the seal surface 20 of the housing 14.

The conical piece 23 has a liquid channel 11 passing through it, being complementary in shape and diameter to liquid channels 11 in an inlet connection 36 not shown in FIGS. 3 and 4, to the connection pieces 50, and to the housing 14. The two end openings of the liquid channel 11 situated in the conical piece 23 are arranged respectively in the outer wall 22 of the conical piece 23.

The conical piece 23 comprises two transverse grooves 24, situated opposite each other on the outer wall 22 of the conical piece 23. The transverse grooves 24, as can be seen, have a straight groove bottom 26. Thus, they do not extend concentrically about the axis of rotation of the plug 16, but rather run as a fluting on the side of the conical piece 23. The two transverse grooves 24 have a roughly funnel-shaped cross section.

The plug 16 moreover comprises a first annular groove 28, situated in the longitudinal direction on the side of the transverse grooves 24 facing toward the handle 33 or on the side of the transverse grooves 24 having a larger diameter than the other side of the transverse grooves 24. The grooves (annular groove 28 and transverse grooves 24) are situated on the side of the liquid channel 11 where the conical piece 23 has a smaller diameter. The annular groove 28, as can be seen, runs concentrically about the axis of rotation of the plug 16. The first annular groove 28 has a roughly funnel-shaped cross section. The cross-sectional area of the annular groove 28 and the transverse grooves 24 (measured for the transverse grooves 24 at their middle) is nearly identical in the embodiment shown. The cross-sectional area is sufficient to accommodate one segment of the spring element 15.

FIGS. 5 and 7 show schematic cross-sectional side views of the stopcock 10 according to the invention, the stopcock being in the working position and the open position (FIG. 5) or the stopcock being in the medium access position and the open position. The open position here denotes the position in which (in the working position) a maximum flow volume can flow through the liquid channel 11 of the left connection piece 50, the stopcock 10 and the right connection piece 50. Thus, the stopcock in the open position is open for the flow of liquid. In the working position shown in FIG. 5, the plug 16 has been pushed tightly into the housing 14. The conical surface 18 of the plug 16 lies tightly against the seal surface 20 of the housing 14. In the medium access position shown in FIG. 7, the plug 16 has been pulled out from the housing 14 such that a gap 48 is formed between the conical piece 23 and the interior of the housing, through which cleaning and/or sterilization gas can flow. At the same time, the plug 16 continues to be held in a locking manner in the housing 14.

The housing 14 comprises connection pieces 50 at either end in the longitudinal direction, making possible a connection to an inlet connection or to another part of the endoscope. For this, one or both connection pieces may have locking elements 52, for example, being shown schematically in the figures. The housing 14, as well as the conical piece 23 of the plug 16, has an elongated liquid channel 11 passing through it. Furthermore, the housing 14 has a recess 56 transversely to the longitudinal direction of the liquid channel 11, having a substantially conical shape and being complementary in size and shape to the conical piece 23 at least for a section.

The plug 16 corresponds to the plug shown in FIGS. 3 and 4. It is locked by means of a spring element 15 in the housing in both the working position (FIG. 5) and in the medium access position (FIG. 7). This prevents the plug 16 from dropping out of the housing 14, for example during the cleaning. In the working position shown in FIG. 5, the spring element 15 engages for this purpose with the first annular groove 28 of the plug 16; in the medium access position shown in FIG. 7, the spring element 15 engages with both transverse grooves 24 from opposite directions, i.e. from opposite sides. The spring force of the spring element 15 thus acts in the direction of the axis of rotation of the plug. This ensures that the plug 16 can only be moved by exerting a rather large force through rotation about the axis of rotation L from the open to the closed position and vice versa, and by exerting pressure along the longitudinal axis from the working position to the medium access position. The spring element 15 is secured to the housing 14 in a manner not shown.

Figure 6:
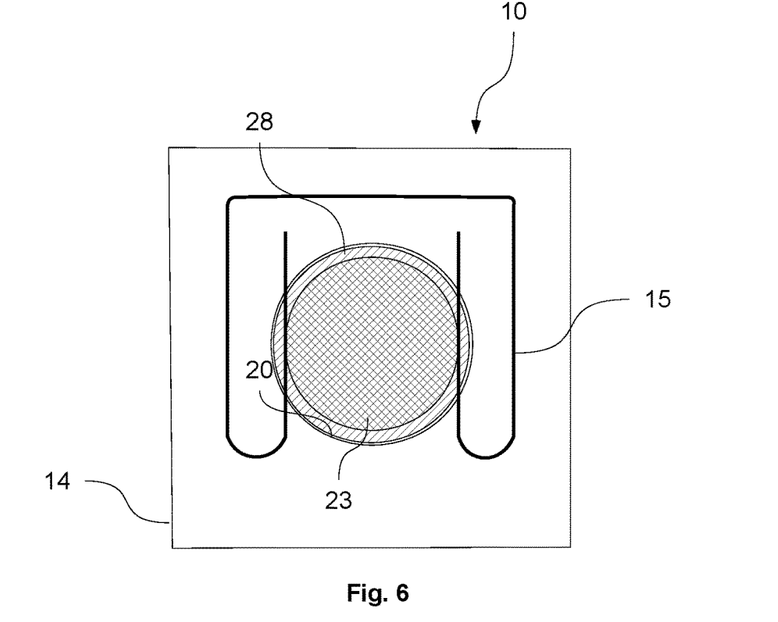
FIG. 6 a schematic cross-sectional side view of the stopcock according to the invention from the viewpoint of the handle part of the plug at the height of the groove bottom of the first annular groove, the stopcock being in the working position.
Figure 8:
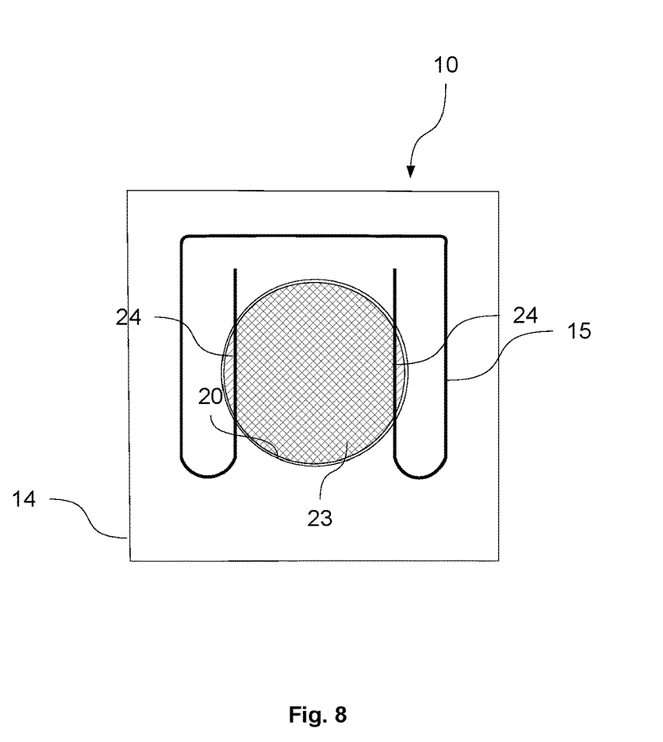
FIG. 8 a schematic cross-sectional side view of the stopcock according to the invention from the viewpoint of the handle part of the plug at the height of the groove bottom of the two transverse grooves, the stopcock being in the medium access position.

The conformation and position of the spring element 15 are explained more closely in FIGS. 6 and 8. The figures show schematic cross-sectional views of the stopcock 10 according to the invention from the viewpoint of the handle part 34 of the plug 16 at the height of the groove bottom of the first annular groove 28, the stopcock 10 being in the working position (FIG. 6), or at the height of the groove bottom of the two transverse grooves 24, the stopcock 10 being in the medium access position (FIG. 8), respectively.

The spring element 15 is configured as a bending spring with a round cross section, i.e. as a metal wire spring. The spring element 15 encloses the conical piece 23 like a bracket. As can be seen in FIG. 6, two pointlike contact areas exist between the spring element 15 and the conical piece 23. In this way, the plug 16 can be rotated more easily from the open position to the closed position in the working position shown in FIG. 6, than in the position shown in FIG. 8. As can be seen in FIG. 8, two line-shaped contact areas exist between the spring element 15 and the conical piece 23. The two end regions of the spring element 15 engage here with the two transverse grooves 24. Thanks to the longer contact area and the angled transition between the ends of the transverse grooves 24 and the conical segments of the plug 16, the plug 16 is much more difficult to rotate from the open position to the closed position in the medium access position shown in FIG. 8, than in the position shown in FIG. 6.

Figure 9:
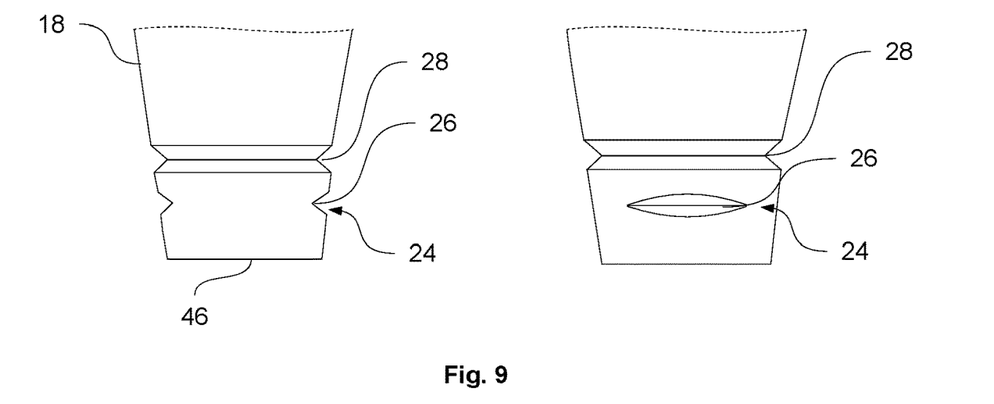
FIG. 9 a schematic side view of the end region of the plug in one embodiment, having two transverse grooves, (left) and a schematic side view of this embodiment rotated by 90° (right)
Figure 10:
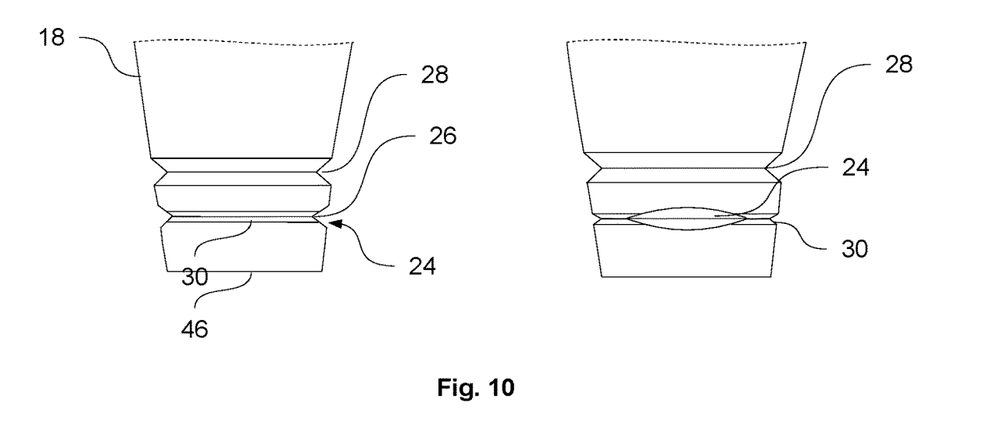
FIG. 10 a schematic side view of the end region of the plug in one embodiment, having two transverse grooves passing into a second annular groove, (left) and a schematic side view of this embodiment rotated by 90° (right)
Figure 11:
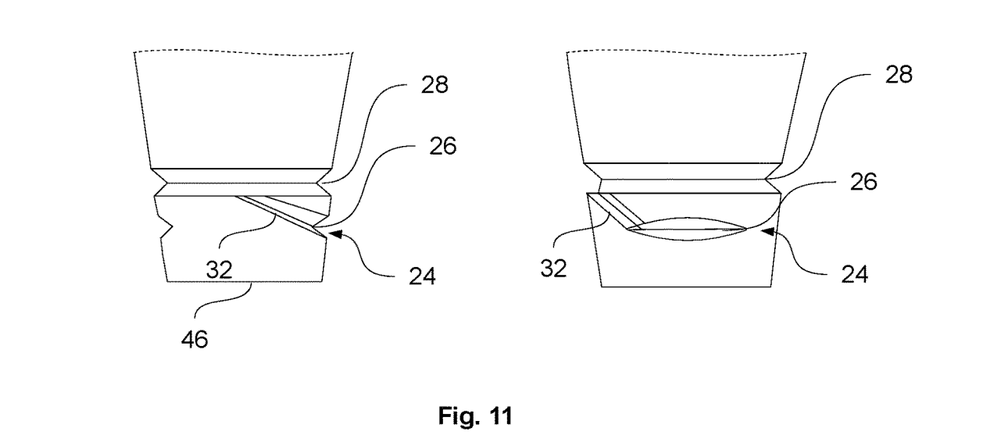
FIG. 11 a schematic side view of the end region of the plug in one embodiment, having two transverse grooves and corresponding connection grooves, (left) and a schematic side view of this embodiment rotated by 90° (right)

FIGS. 9 to 11 show schematic side views of the end region of the plug 16 in three different embodiments. Each time, the left side of the figures shows a side view of the end region and the right side of the figures shows a schematic side view of the same embodiment, rotated by 90°.

FIG. 9 shows an embodiment in which the plug 16 comprises two transverse grooves 24. Thus, this embodiment corresponds to the embodiment shown in FIGS. 3 to 8. The ends of the transverse grooves 24 pass directly into a conical segment of the plug 16. The transverse grooves 24 are entirely surrounded by conical surfaces.

By contrast with this, FIG. 10 shows an embodiment in which the two transverse grooves 24 are each formed as segments of a second annular groove 30, the second annular groove 30 running concentrically about the axis of rotation of the plug 16 outside the two transverse grooves 24 and parallel to the first annular groove 28. The groove bottom 26 of the transverse grooves 24 and the groove bottom of the second annular groove 30 are spaced at equal distances from the first annular groove 28.

FIG. 11 shows a schematic side view of the end region of the plug 16 in one embodiment, having two transverse grooves 24 and two connection grooves 32, only one of the two connection grooves 32 being visible. The connection grooves 32 respectively join the end region of the two transverse grooves 24 situated in the direction of rotation to the first annular groove 28. For this purpose, the connection grooves 32 run at a slant to the longitudinal direction and to the direction of rotation of the conical piece 23. The connection grooves 32, upon rotating the plug 16, interact in the manner of a thread. In this way, the spring element 15 can be brought by rotation into the first annular groove 28 from the transverse grooves 24. At the same time, the stopcock 10 is brought from the medium access position to the working position. In this way, a cleaning in the closed position can be prevented.

Figure 12:
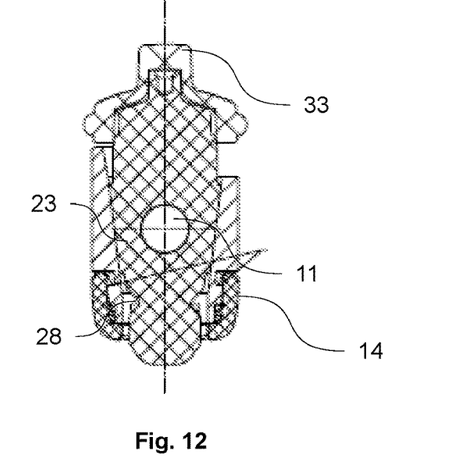
FIG. 12 a schematic side view of an alternative embodiment of the stopcock according to the invention from the viewpoint of the liquid channel, the stopcock being in the working position.
Figure 13:
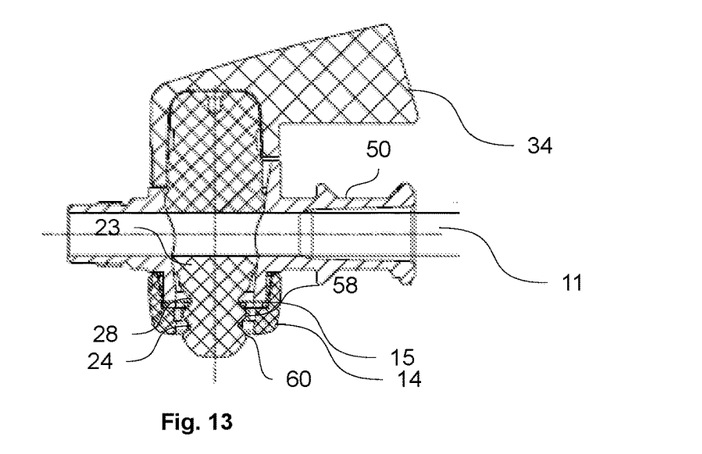
FIG. 13 a schematic cross-sectional view of the embodiment of FIG. 12, rotated by 90° about the axis of rotation of the plug, the stopcock being in the working position.
Figure 14:
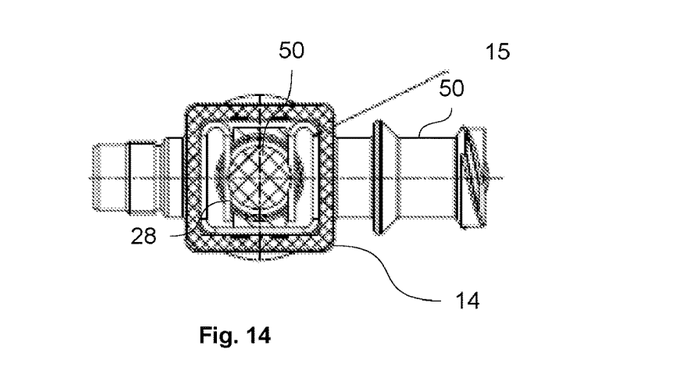
FIG. 14 a schematic cross-sectional view of the embodiment of FIGS. 12 and 13, from the viewpoint of the handle part of the plug at the height of the groove bottom of the first annular groove, the stopcock being in the working position.

FIG. 12 to FIG. 14 show schematic side views of an alternative embodiment of the stopcock 10 according to the invention, the stopcock 10 being in the working position. The cross-sectional views are a side view from the viewpoint of the liquid channel 11 (FIG. 12), a view rotated 90° about the axis of rotation of the conical piece 23 (FIG. 13), and a view from the viewpoint of the handle part 34 of the plug 16 at the height of the groove bottom of the first annular groove 28. The embodiment is based on that in FIG. 9, the conical piece 23 of the plug 16 having a first annular shoulder 58 besides the first annular groove 28 and the transverse groove 24, located between the first annular groove 28 and the transverse groove 24, extending like a ring about the circumference of the conical piece 23. Furthermore, the conical piece 23 has a second annular shoulder 60 on the other side of the transverse groove 24, the side facing away from the handle part 34. In the region of the annular shoulders 58, 60, the conical piece 23 has a larger diameter than in the regions of the grooves. The second annular shoulder 60 secures the plug 16 in the housing 14.

In the embodiment of FIGS. 12 to 14, the plug 16 is two-piece, where the handle 33 and the conical piece 23 are two parts separable from each other. The plug 16, as described elsewhere, is held by means of a spring element 15 in the housing 14 and locked in the working position. For this, the spring element 15 engages with the first annular groove 28.

Although the present invention has been described in detail with the aid of the exemplary embodiments, it is self-evident to the person skilled in the art that the invention is not limited to these exemplary embodiments, but rather modifications are possible such that individual features are left out or other combinations of the individual features shown can be realized as long as one stays within the scope of protection of the accompanying claims. The present disclosure encompasses all combinations of the individual features shown.

The invention claimed is:

1. A stopcock for a liquid channel of a medical endoscope, the stopcock comprising:
    a housing;
    a spring element; and
    a plug rotatably mounted in the housing, the plug comprising:
        a conical piece having a conical outer surface;
        two transverse grooves situated opposite each other in the conical outer surface of the conical piece, the two transverse grooves running transversely to a longitudinal axis of the conical piece and having straight groove bottoms; and
        a first annular groove running concentrically parallel to the two transverse grooves,
    wherein the plug is configured to rotate between the following positions:
        a working position in which:
            the plug lies with its conical outer surface against a seal surface of the housing, and
            the spring element engages with the first annular groove, and
        a medium access position in which:
            the conical outer surface and the seal surface have no contact and the housing and the plug remain connected, and
            the spring element engages with the two transverse grooves.

2. The stopcock according to claim 1, wherein the two transverse grooves are each configured as a segment of a second annular groove, wherein the second annular groove runs concentrically parallel to the first annular groove outside of the two transverse grooves.

3. The stopcock according to claim 1, wherein the plug comprises two connection grooves in the conical outer surface of its conical piece, each of them joining one end of a transverse groove to the first annular groove.

4. The stopcock according to claim 3, wherein the two connection grooves are arranged at a slant to the longitudinal axis of the first annular groove.

5. The stopcock according to claim 1, wherein the two transverse grooves have a trapezoidal cross section.

6. The stopcock according to claim 1, wherein the spring element is a bending spring or an elastomer ring.

7. The stopcock according to claim 6, wherein the bending spring has a round cross section.

8. The stopcock according to claim 1, wherein the two transverse grooves do not extend concentrically about the longitudinal axis of the conical piece.

9. The stopcock according to claim 1, wherein the two transverse grooves have a funnel-shaped cross section.

10. A medical endoscope having at least one liquid channel, the medical endoscope comprising at least one stopcock according to claim 1, by means of which the liquid flow through the liquid channel can be regulated.

\* \* \* \* \*